United States Patent [19]

Krüger et al.

[11] Patent Number: 4,567,168

[45] Date of Patent: Jan. 28, 1986

[54] CYANOHYDRIN PHOSPHONATES AS PESTICIDES

[75] Inventors: Bernd-Wieland Krüger; Hans-Jochem Riebel, both of Wuppertal; Ingeborg Hammann, Cologne; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 344,268

[22] Filed: Jan. 28, 1982

[30] Foreign Application Priority Data

Feb. 21, 1981 [DE] Fed. Rep. of Germany ....... 3106475
Nov. 12, 1981 [DE] Fed. Rep. of Germany ....... 3145009

[51] Int. Cl.[4] .......................... C07F 9/40; A01N 57/02
[52] U.S. Cl. ......................................... 514/89; 546/22; 549/218; 549/221; 549/6; 514/99; 514/101; 514/112; 260/940
[58] Field of Search .................. 260/940; 514/112, 99, 514/101, 89

[56] References Cited

U.S. PATENT DOCUMENTS 2,965,533 12/1960 Whetstone ........................... 424/210
3,927,148 12/1975 Oswald et al. ....................... 260/948
4,496,493 1/1985 Hodakowski et al. ............... 260/940

FOREIGN PATENT DOCUMENTS 0044214 1/1982 European Pat. Off. .
1047776 12/1958 Fed. Rep. of Germany .
1224307 9/1966 Fed. Rep. of Germany ...... 260/940

OTHER PUBLICATIONS

Chemical Abstracts, vol. 69, 1968, 67489j.
Journal of General Chemistry of USSR, V. E. Shishkin, et al., pp. 2369-2371.
Synthesis-International Journal of Methods etc., Mar. 1978, pp. 219-220.

Primary Examiner—Anton H. Sutto

Attorney, Agent, or Firm—Sprung Horn Kramer & Woods

[57] ABSTRACT

A cyanohydrin phosphate of the formula

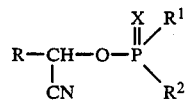

(I)

wherein
R represents a hydrogen atom or an optionally substituted radical selected from alkyl, alkenyl, alkynyl, cycloalkyl, cycloalkenyl, aralkyl, aralkenyl and aryl, or an optionally substituted heterocyclic radical,
$R^1$ and $R^2$ are identical or different and individually represent optionally substituted radicals selected from alkyl, alkenyl, alkynyl, aryl, aralkyl, alkoxy, aryloxy, aralkoxy, alkylthio, alkenylthio, alkinylthio, arylthio, aralkylthio, alkylamino (monoalkylamino or dialkylamino), arylamino and aralkylamino, or together represent alkanediyl, alkanedioxy, aminoalkyloxy or alkanediamino, and
X represents oxygen or sulphur,
are obtained by the reaction of a phosphoric acid chloride of the general formula

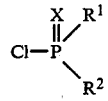

(II)

wherein X, $R^1$ and $R^2$ have the meaning given above, with an aldehyde of the general formula

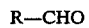

(III)

wherein R has the meaning given above, in the presence of an approximately equimolar quantity of water-soluble cyanides. Some of the compounds of the formula (I) are new. They can be used as insectides and acaricides.

11 Claims, No Drawings

CYANOHYDRIN PHOSPHONATES AS PESTICIDES

The invention relates to an unobvious process for the production of certain cyanohydrin phosphates, to certain new cyanohydrin phosphates, to an unobvious process for their production and to their use as pesticides, in particular as insecticides and acaricides.

It is already known that particular cyanohydrin phosphates which can be used for combating pests are obtained if appropriate phosphoric acid ester chlorides are reacted with cyanohydrins (α-hydroxy-carboxylic acid nitriles) (see Deutsche Auslegeschriften (German Published Specifications) Nos. 1,047,776 and 1,223,307). In this process, however, the desired compounds are mostly obtained in low yields; the pesticidal action of the previously known cyanohydrin phosphates is, in addition, unsatisfactory.

Furthermore, it is known that particular cyanohydribn phosphates can also be prepared if the cyanohydrins are produced in situ, in the reaction mixture, from carbonyl compounds and alkali metal cyanides, and are reacted, without intermediate isolation, with phosphoric acid ester chlorides (see U.S. Pat. No. 2,965,533). However, this process is time-consuming and/or yields only moderate yields.

According to the present invention we provide a process for the production of a cyanohydrin phosphate of the general formula

in which
R represents a hydrogen atom, an optionally substituted radical selected from alkyl, alkenyl, alkynyl, cycloalkyl, cycloalkenyl, aralkyl, aralkenyl and aryl, or an optionally substituted heterocyclic radical, $R^1$ and $R^2$ are identical or different and individually represent optionally substituted radicals selected from alkyl, alkenyl, alkynyl, aryl, aralkyl, alkoxy, aryloxy, aralkoxy, alkylthio, alkenylthio, alkinylthio, arylthio, aralkylthio, alkylamino(monoalkylamino) or dialkylamino), arylamino and aralkylamino, or together represent alkanediyl, alkanedioxy, aminoalkyloxy or alkanediamino and X represents oxygen or sulphur,
characterized in that a phosphoric acid chloride of the general formula

in which X, $R^1$ and $R^2$ have the meaning given above, is reacted with an aldehyde of the general formula

R—CHO (III)

in which R has the meaning given above, in the presence of an approximately equimolar quantity of a water-soluble cyanide, in the presence of a catalyst, and in the presence of water and a solvent, which is a virtually water-immiscible hydrocarbon, at a temperature between 0° and 80° C.

The cyanohydrin phosphates produced by the process of the present invention are obtained in a short reaction time, in very good yield and in high purity.

The present invention further provides, as new compounds, cyanohydrin phosphates of the general formula

in which
R' represents a hydrogen atom or an optionally substituted radical selected from alkyl, alkenyl, alkynyl, cycloalkyl, aralkyl and aryl, or represents an optionally substituted heterocyclic radical, $R^{1'}$ represents an optionally substituted radical selected from alkoxy, aryloxy, aralkoxy, alkylthio, alkenylthio, alkinylthio, arylthio, aralkylthio, alkylamino (monoalkylamino or dialkylamino), arylamino and aralkylamino, $R^{2'}$ represents an optionally substituted radical selected from alkyl, aryl, aralkyl, aryloxy, aralkoxy, alkylthio, alkenylthio, alkinylthio, arylthio, aralkylthio, alkylamino (monoalkylamino or dialkylamino) arylamino and aralkylamino, and X represents oxygen or sulphur.

According to the present invention we further provide a process for the production of the novel cyanohydrin phosphates of formula (Ia) of the present invention, characterized in that a phosphoric acid chloride of the general formula

in which
$R^{1'}$ and $R^{2'}$ have the meaning given above and
X represents oxygen or sulphur,
is reacted with an aldehyde of the general formula R'—CHO (IIIa)

in which
R' has the meaning given above, in the presence of an approximately equimolar quantity of a water-soluble cyanide, in the presence of a catalyst, and in the presence of water and a solvent, which is a virtually water-immiscible hydrocarbon, at a temperature between 0° and 80° C.

Optionally substituted alkyl of R, R', $R^1$, $R^2$ and $R^{2'}$ are normally straight-chain or branched alkyl having 1 to 20, preferably 1 to 10, particularly 1 to 5, carbon atoms. Optionally substituted methyl, ethyl, n-propyl, i-propyl, n-butyl, i-butyl and t-butyl may be mentioned as examples.

Optionally substituted alkenyl of R, R', $R^1$ and $R^2$ and optionally substituted alkenylthio $R^1$, $R^2$, $R^{1'}$ and $R^{2'}$ are straight-chain or branched radicals having preferably 2 to 5, particularly 2 to 4, carbon atoms.

Optionally substituted ethenyl, propen-1-yl, propen-2-yl and buten-3-yl and the respective thio-radicals may be mentioned as examples.

Optionally substituted alkynyl of R, R', $R^1$ and $R^2$ and optionally substituted alkynylthio $R^1$, $R^2$, $R^{1'}$ and $R^{2'}$ are straight-chain or branched radicals having preferably 2 to 5, particularly 2 to 4, carbon atoms.

Optionally substituted ethynyl, propyn-1-yl, propyn-2-yl and butyn-3-yl and the respective thio-radicals may be mentioned as examples.

Optionally substituted cycloalkyl of R and R' are monocyclic, bicyclic and tricyclic cycloalkyl having preferably 3 to 8, particularly 3, 5 or 6 carbon atoms. Optionally substituted cyclopropyl, cyclobutyl, cyclopentyl, cyclohexyl, cycloheptyl, bicyclo-[2.2.1]-heptyl, bicyclo-[2.2.2]-octyl and adamantyl may be mentioned as examples.

Optionally substituted cycloalkenyl of R is preferably monocyclic cycloalkenyl having 5 or 6 carbon atoms and 1 or 2 double bonds.

Optionally substituted alkoxy of $R^1$, $R^{1'}$ and $R^2$ are straight-chain or branched alkoxy having preferably 1 to 6, particularly 1 to 4 carbon atoms. Optionally substituted methoxy, ethoxy, n-propoxy, i-propoxy, n-butoxy, i-butoxy and t-butoxy may be mentioned as examples.

Optionally substituted alkylthio of $R^1$, $R^{1'}$, $R^2$ and $R^{2'}$ are straight-chain or branched alkylthio having preferably 1 to 6, particularly 1 to 4, carbon atoms. Optionally substituted methylthio, ethylthio, n-propylthio, i-propylthio, n-butylthio, i-butylthio and t-butylthio may be mentioned as examples.

Optionally substituted aryl of R, R', $R^1$, $R^2$ and $R^{2'}$ are aryl having preferably 6 to 10 carbon atoms in the aryl part. Optionally substituted phenyl or naphthyl, particularly phenyl, may be mentioned as an example.

Optionally substituted aralkyl of R, R', $R^1$, $R^2$ and $R^{2'}$ are aralkyl which is optionally substituted in the aryl part and/or alkyl part and which preferably has 6 or 10, particularly 6, carbon atoms in the aryl part and preferably 1 to 4, particularly 1 or 2, carbon atoms in the alkyl part, it being possible for the alkyl part to be straight-chain or branched. Optionally substituted benzyl and phenylethyl may be mentioned as examples.

Optionally substituted aralkenyl of R corresponds in its aryl part with the aralkyl radical R. It contains, in the alkenyl part, preferably 2 to 6, particularly 2 or 3, carbon atoms, and preferably one double bond.

Optionally substituted aryloxy, arylthio and arylamino of $R^1$, $R^{1'}$, $R^2$ and $R^{2'}$ preferably contain 6 or 10 carbon atoms in the aryl part, phenyloxy, naphthyloxy, phenylthio, naphthylthio, phenylamino and naphthylamino, preferably phenyloxy, phenylthio and phenylamino, being mentioned.

Optionally substituted aralkoxy, aralkylthio and aralkylamino of $R^1$, $R^{1'}$, $R^2$ and $R^{2'}$ contain, in the aryl part, preferably 6 or 10 carbon atoms, phenyl being mentioned as particularly preferred. The alkyl part is branched or straight-chain and contains preferably 1 to 4, particularly 1 or 2, carbon atoms. The benzyl radical is particularly preferred as the aralkyl part.

In the optionally substituted alkylamino of $R^1$, $R^{1'}$, $R^2$ and $R^{2'}$, the amino group contains 1 or 2 alkyl groups, each of which can be straight-chain or branched and preferably contain 1 to 5, particularly 1 to 3, carbon atoms, methyl, ethyl, n-propyl and i-propyl being mentioned. Methylamino and dimethylamino may be quoted as examples.

Optionally substituted heterocyclic radicals of R and R' are heteroparaffinic, heteroaromatic and heteroolefinic 5-membered to 7-membered, preferably 5-membered or 6-membered, rings having preferably 1 to 3, particularly 1 or 2, identical or different hetero-atoms. Oxygen, sulphur or nitrogen are hetero-atoms. Optionally substituted pyrrolidinyl, piperidinyl, furyl, thiophenyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,3,4-oxadiazolyl, 1,2,4-oxadiazolyl, 1,2,5-oxadiazolyl, azepinyl, pyrrolyl, pyridyl, piperazinyl, pyridazinyl, pyrimidinyl, pyrazinyl, 1,3,5-triazinyl, 1,2,4-triazinyl, 1,2,3-triazinyl, 1,2,4-oxazinyl, 1,3,2-oxazinyl, 1,3,6-oxazinyl, 1,2,6-oxazinyl, oxepinyl, thiepinyl and 1,2,4-diazepinyl may be mentioned as examples.

The substituted radicals mentioned in the definition of R, R', $R^1$, $R^{1'}$, $R^2$ and $R^{2'}$ can carry one or more, preferably 1 to 3, particularly 1 or 2, identical or different substituents. The following may be quoted as examples of substituents: alkyl having preferably 1 to 4, particularly 1 or 2, carbon atoms, such as methyl, ethyl, n-propyl, i-propyl, n-butyl, i-butyl and t-butyl; alkoxy having preferably 1 to 4, particularly 1 or 2, carbon atoms, such as methoxy, ethoxy, n-propyloxy, i-propyloxy, n-butyloxy, i-butyloxy and t-butyloxy; alkylthio having preferably 1 to 4, particularly 1 or 2, carbon atoms, such as methylthio, ethylthio, n-propylthio, i-propylthio, n-butylthio, i-butylthio and t-butylthio; alkylamino having 1 or 2 alkyl groups each of which contains preferably 1 to 4, particularly 1 or 2 carbon atoms, such as monomethylamino, dimethylamino, monoethylamino and diethylamino; halogenoalkyl, halogenoalkylthio and halogenoalkoxy each having preferably 1 to 4, particularly 1 or 2, carbon atoms and preferably 1 to 5, particularly 1 to 3, halogen atoms, the halogen atoms being identical or different and preferably being fluorine, chlorine or bromine, particularly fluorine, such as trifluoromethyl, trifluoromethoxy and trifluoromethylthio; halogen, preferably fluorine, chlorine, bromine and iodine, particularly chlorine and bromine; nitro; alkoxycarbonyl having preferably 2 to 4, particularly 2 or 3, carbon atoms, such as methoxycarbonyl and ethoxycarbonyl; and phenoxybenzyloxycarbonyl. In the case of radicals containing aryl parts, the aryl parts, for example the phenyl rings, can be substituted by alkylenedioxy groups which contain preferably 1 to 3, particularly 1 or 2, carbon atoms and can be substituted by 1 to 4 identical or different halogen atoms (fluorine, chlorine, bromine and iodine).

- Halogen denotes (if not otherwise indicated) fluorine, chlorine, bromine and iodine, preferably fluorine, chlorine and bromine.

Alkanediyl radicals, alkanedioxy radicals, aminoalkoxy radicals or alkanediamino radicals in the definition of $R^1$ and $R^2$ contain preferably 1 to 3, particularly 1 or 2, carbon atoms.

The new cyanohydrin phosphates of the formula (Ia) are distinguished by a high activity against animal pests, particularly by high insecticidal and acaricidal activity. They can also be used in synergistic mixtures with other pesticides. Some of them also exhibit a fungicidal action, particularly against Piricularia oryzae in rice.

Surprisingly, the compounds, according to the invention, of the formula (Ia) exhibit a considerably greater insecticidal and acaricidal action than known compounds of analogous constitution and identical direction of action. It is also surprising that the compounds of the formula (I) are obtained by the process according to the invention in a short reaction time, in very good yields, and in high purity.

Preferred compounds of the formula (Ia) according to the present invention are those in which R' represents a hydrogen atom, an alkyl radical which is optionally substituted by halogen, $C_1$ to $C_4$ alkoxy, $C_1$ to $C_4$ alkylthio or $C_1$-$C_4$-alkylamino and which has 1 to 20 carbon atoms, an optionally halogen-substituted $C_2$ to $C_5$ alkenyl or $C_2$ to $C_5$ alkynyl radical, a $C_3$ to $C_8$ cycloalkyl radical which is optionally substituted by $C_1$ to $C_4$ alkyl, $C_2$ to $C_4$ alkoxycarbonyl, phenoxybenzyloxycarbonyl and/or halogen, a phenyl-$C_1$ or $C_2$ alkyl radical which is optionally substituted by halogen, optionally halogen-substituted $C_1$ to $C_4$ alkyl or optionally halogen substituted $C_1$ to $C_4$ alkoxy, a phenyl radical which is optionally substituted by halogen, nitro, $C_1$ to $C_4$ alkyl, optionally halogen-substituted $C_1$ to $C_4$ alkoxy, optionally halogen-substituted $C_1$ to $C_4$ alkylthio, trifluoromethyl and/or by optionally halogen substituted $C_1$ or $C_2$ alkylenedioxy, or a furyl, thienyl or pyridyl radical, $R^{1'}$ represents an optionally halogen-substituted radical selected from $C_1$ to $C_5$ alkoxy, phenoxy, benzyloxy, $C_1$ to $C_5$ alkylthio, $C_3$ to $C_5$ alkenylthio, $C_3$ to $C_5$ alkynylthio, phenylthio, benzylthio and $C_1$ to $C_5$ alkylamino (monoalkylamino or dialkylamino), $R^{2'}$ represents an optionally halogen- or $C_1$ to $C_4$ alkylthio-substituted radical selected from $C_1$ to $C_5$ alkyl, phenyl, phenoxy, benzyloxy, $C_1$ to $C_5$ alkylthio, $C_3$ to $C_5$ alkenylthio, $C_3$ to $C_5$ alkynylthio, phenylthio, benzylthio and $C_1$ to $C_5$ alkylamino (monoalkylamino or dialkylamino), and X represents oxygen or sulphur.

In these definitions, halogen denotes, in each case, fluorine, chlorine, bromine and iodine, preferably fluorine, chlorine and bromine.

Particularly preferred compounds of the formula (Ia) of the present invention are those in which R' represents a hydrogen atom, an alkyl radical which is optionally substituted by fluorine, chlorine, methoxy, methylthio or dimethylamino and which has 1 to 10 carbon atoms, a $C_2$ to $C_5$ alkenyl, a $C_3$ to $C_6$ cycloalkyl radical which is optionally substituted by chlorine and/or methyl, a phenyl-$C_1$ or $C_2$ alkyl radical which is optionally substituted by chlorine or trifluoromethoxy, a phenyl radical which is optionally substituted by fluorine, chlorine, nitro, methyl, methoxy, trifluoromethoxy, trifluoromethyl, and/or methylenedioxy, a thienyl radical or a pyridyl radical, $R^{1'}$ represents an optionally fluorine-substituted or chlorine-substituted radical selected from $C_1$ to $C_5$ alkoxy, phenoxy, benzyloxy, $C_1$ to $C_5$ alkylthio and $C_1$ to $C_5$ alkylamino (monoalkylamino or dialkylamino), $R^{2'}$ represents an optionally fluorine- or chlorine- or ethylthio-substituted radical selected from $C_1$ to $C_5$ alkyl, phenyl, phenoxy, $C_1$ to $C_5$ alkylthio, phenylthio, benzylthio and $C_1$ to $C_5$ alkylamino (monoalkylamino or dialkylamino), and X represents oxygen or sulphur.

If, for example, O-ethylthionomethanephosphonic acid ester chloride, propionaldehyde and potassium cyanide are used as starting materials in the process according to the invention, the reaction of these compounds can be represented by the following equation:

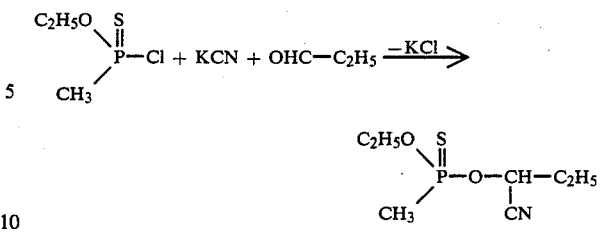

Preferred phosphoric acid chlorides of formula (II) to be used as starting materials in the process according to the invention are those in which X, $R^1$ and $R^2$ represent those radicals which are given above in the definition of the corresponding radicals X, $R^{1'}$ and $R^{2'}$ in preferred or particularly preferred compounds of formula (Ia) and $R^2$ also preferably represents $C_1$ to $C_5$ alkoxy.

The following may be mentioned as examples of the compounds of the formula (II): O-methyl-, O-ethyl-, O-n-propyl- and O-iso-propyl-methane-, ethane-, propane- and benzene-phosphonic acid ester chloride and the corresponding thiono analogues, O,O-dimethyl-, O,O-diethyl-, O,O-di-n-propyl-, O-methyl-O-ethyl-, O-methyl-O-n-propyl-, O-methyl-O-iso-propyl-, O-ethyl-O-n-propyl- and O-ethyl-O-iso-propylphosphoric acid diester chloride and the corresponding thiono analogues, or O,S-dimethyl-, O,S-diethyl-, O,S-di-n-propyl-, O,S-di-iso-propyl-, O-methyl-S-ethyl-, -methyl-S-n-propyl-, O-methyl-S-iso-propyl-, O-ethyl-S-methyl-, O-ethyl-S-n-propyl-, O-ethyl-S-iso-propyl-, O-n-propyl-S-methyl-, O-n-propyl-S-ethyl-, O-n-propyl-S-iso-propyl-, O-iso-propyl-S-methyl-, O-iso-propyl-S-ethyl- and O-iso-propyl-S-n-propylthiolphosphoric acid diester chloride, and the corresponding thiono analogues, or O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-propyl-N-methyl-, O-n-propyl-N-ethyl-, O-n-propyl-N-n-propyl-, O-n-propyl-N-iso-propyl-, O-iso-propyl-N-methyl-, O-iso-propyl-N-ethyl-, O-iso-propyl-N-n-propyl- and O-iso-propyl-N-iso-propylphosphoric acid ester amide chloride and the corresponding thiono analogues, or S-n-propyl-N-iso-propyl-thionothiol-phosphoric acid ester amide chloride, O-ethyl-S-benzyl-thionothiol-phosphoric acid diester chloride, S-sec.-butyl-thionothiol-ethanephosphonic acid ester chloride, S-n-propyl-thionothiol-methanephosphonic acid ester chloride, S-n-propyl-thionothiol-chloromethanephosphonic acid ester chloride, O-ethyl-O-(4-chlorophenyl)-thionophosphoric acid diester chloride, O-(2,2,2-trifluoroethyl)-thionomethanephosphonic acid ester chloride and O-(2,2,2-trifluoroethyl)-S-n-propyl-thionothiol-phosphoric acid diester chloride.

Compounds of the formula (II) are known and can be prepared by processes which are in themselves known (see Methoden der organischen Chemie (Methods of Organic Chemistry) (Houben-Weyl-Müller), 4th edition, volume 12/1 (1963), pages 415–420 and pages 560–563; volume 12/2 (1964), pages 274–292 and pages 607–618; Thieme-Verlag Stuttgart).

Preferred aldehydes of formula (III) which are also to be used as starting materials are those in which R represents those radicals which are given above in the definition of R' in preferred and particularly preferred compounds of formula (Ia).

The following may be mentioned as examples of the compounds of the formula (III): formaldehyde, acetaldehyde, propionaldehyde, butyraldehyde, iso-butyraldehyde, valeraldehyde, iso-valeraldehyde, sec.-valeraldehyde, caproaldehyde, iso-caproaldehyde, sec.-caproaldehyde, pivalic aldehyde, acrolein, crotonaldehyde, methoxyacetaldehyde, methylthioacetaldehyde, cyclohexanecarbaldehyde, benzaldehyde, 4-chloro-benzaldehyde, 4-methyl-benzaldehyde, 3,4-methylenedioxy-benzaldehyde, 4,5-methylenedioxy-2-nitro-benzaldehyde, phenylacetaldehyde, α-phenylpropionaldehyde, thiophene-2-carbaldehyde, thiophene-3-carbaldehyde, pyridine-2-carbaldehyde and pyridine-3-carbaldehyde.

The starting compounds of the formula (III) are known.

Alkali metal cyanides (such as sodium cyanide and potassium cyanide) are examples of water-soluble cyanides which can be used in the process according to the invention; sodium cyanide is preferably used.

Straight-chain or branched alkanes or cycloalkanes having 5 to 10 carbon atoms (such as n-pentane, n-hexane, n-heptane, n-octane, n-nonane, n-decane, 2-methylpentane, 3-methylpentane, 2-methylhexane, 2,2,4-trimethylpentane, cyclohexane and methylcyclohexane) or also methylbenzenes (such as toluene, or xylenes) and also mixtures of these hydrocarbons are preferably employed as water-immiscible solvents in the process according to the invention.

Compounds which are customarily used for the phase transfer of reactants in reactions in two-phase systems composed of water and water-immiscible organic solvents are preferably used as the catalysts in the process according to the invention. Tetraalkylammonium salts and trialyl-aralkylammonium salts having preferably 1 to 10, particularly 1 to 8, carbon atoms per alkyl group, preferably phenyl as the aryl constituent of the aralkyl groups and preferably 1 to 4, particularly 1 or 2, carbon atoms in the alkyl part of the aralkyl groups, are especially preferred as such catalysts. The halides, such as chlorides, bromides and iodides, preferably the chlorides and bromides, are especially suitable in this context. Tetrabutylammonium bromide, benzyl-triethylammonium chloride and methyl-trioctylammonium chloride may be mentioned as examples.

In the process according to the invention, the reaction temperature is kept between 0° and 80° C., preferably between 0° and 30° C. The process is preferably carried out under normal pressure.

In general, between 0.8 and 1.2 mols, preferably 0.9 to 1.1 mols, of aldehyde of the formula (III), between 1.0 and 1.5 mols, preferably 1.1 to 1.3 mols, of cyanide and between 0.001 and 0.05 mol, preferably 0.01 to 0.03 mol, of catalyst are employed per mol of phosphoric acid chloride of the formula (II).

In a preferred embodiment of the process according to the invention, the starting compounds of the formulae (II) and (III) and the catalyst are dissolved in the water-immiscible solvent, and an aqueous solution of the cyanide is slowly added to this solution, if necessary the reaction temperature being brought to 0° to 10° C. at first by external cooling. The complete reaction mixture is then stirred, without cooling, until the end of the reaction.

To work up the mixture, it is diluted, if necessary, with more water-immiscible solvent, and the organic phase is separated off, washed with water, dried and filtered. The filtrate is freed from solvent by ditillation under reduced pressure, the crude product being obtained as an oleaginous residue. The refractive index serves to characterize the product.

The active compounds are well tolerated by plants, have a favorable level of toxicity to warm-blooded animals, and can be used for combating arthropod pests, especially insects and arachnida which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemoineata, Phaedon cochleariae, Diabrotica spp., Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aendus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp., The new active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cams, fumigating coils and the like, as well as ULV cold mist and warm mist formulations.

These formulations may be produced in knownmanner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations, It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds ae distinguished by an excellent residual action on wood and clay as well as a good stability to alkali on limed substrates.

The active compounds according to the invention are also suitable for combating ectoparasites and endoparasites in the field of animal husbandry and animal breeding, it being possible to achieve better results, for example higher milk yields, higher weight, longer life-span, etc., by combating the pests.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects or acarids) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

The active compounds according to the invention may be used in a known manner in these fields, such as by oral administration, for example in the form of tablets, capsules, drinks and granules, by dermal application, for example by means of dipping, spraying, pouring-on and spotting-on, and dusting, and by parenteral administration, for example by means of an injection.

The process according to the invention is illustrated by the following example:

EXAMPLE 1

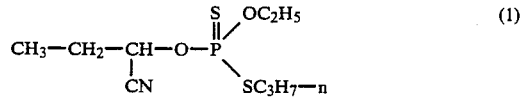     (1)

11.6 g (0.2 mol) of propanal, 43.7 g (0.2 mol) of O-ethyl-S-propyl-dithiophosphoric acid diester chloride and 1.2 g of tetrabutylammonium bromide were initially introduced into 300 ml of hexane, and a solution of 11.2 g (0.23 mol) of sodium cyanide in 20 ml of water was added dropwise to the mixture at an internal temperature between 0° and 10° C., while stirring vigorously. After the addition had ended, the temperature was slowly increased to 20° C. and the mixture was further stirred until the end of the reaction. The aqueous phase was then separated off, and the organic phase was washed twice with 100 ml of water and dried over sodium sulphate. After the solvent had been stripped off in the vacuum from a water jet and less volatile constituents had been distilled off at 50° C./3 mbars, 50.5 g (95% of theory) of O-ethyl-O-(1-cyanopropyl)-S-propyldithiophosphoric acid ester of refractive index $n_D^{20}$: 1.5120 were obtained as an oleaginous residue.

The compounds which are listed in the table below and are of the formula

     (I)

could be prepared analogously:

TABLE

| Compound No. | R | $R^1$ | $R^2$ | X | Refractive index ($n_D^{20}$) |
|---|---|---|---|---|---|
| 2 | —CH$_2$—SCH$_3$ | —OC$_2$H$_5$ | —SC$_3$H$_7$—n | S | 1.5336 |
| 3 | —C$_3$H$_7$—iso | —SC$_3$H$_7$—n | —NH—C$_3$H$_7$—iso | S | 1.5160 |
| 4 | 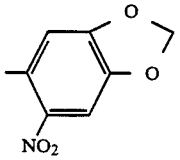 | —OC$_2$H$_5$ | —SC$_3$H$_7$—n | S | 1.5762 |
| 5 | —CH$_3$ | —OC$_2$H$_5$ | —OC$_2$H$_5$ | S | 1.4664 |
| 6 | —C$_3$H$_7$—iso | —SC$_3$H$_7$—n | —OCH$_2$CF$_3$ | S | 1.4799 |
| 7 | —CH—CH$_2$CH$_2$CH$_3$<br>    |<br>  CH$_3$ | —OC$_2$H$_5$ | —SC$_3$H$_7$—n | S | 1.4950 |
| 8 | —CH$_2$OCH$_3$ | —OC$_2$H$_5$ | —SC$_3$H$_7$—n | S | 1.5109 |
| 9 | 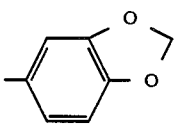 | —OC$_2$H$_5$ | —SC$_3$H$_7$—n | S | 1.5480 |

| | R | $R^1$ | $R^2$ | X | Refractive index ($n_D^{20}$) |
|---|---|---|---|---|---|
| 10 | —$C_3H_7$—iso | —$OC_2H_5$ | —$SCH_2$—C₆H₅ | S | 1.5412 |
| 11 | —CH(CH₃)—C₆H₅ | —$C_2H_5$ | —S—CH(CH₃)—CH₂CH₃ | S | 1.5496 |
| 12 | —CH(CH₃)—C₆H₅ | —$CH_3$ | —$SC_3H_7$—n | S | 1.5583 |
| 13 | —CH(CH₃)—C₆H₅ | —$CH_2Cl$ | —$SC_3H_7$—n | S | 1.5618 |
| 14 | —CH(CH₃)—C₆H₅ | —$OC_2H_5$ | —$SC_3H_7$—n | O | 1.5155 |
| 15 | cyclohexyl (H) | —$OC_2H_5$ | —$SC_3H_7$—n | S | 1.5135 |
| 16 | —$C_3H_7$—iso | —$OC_2H_5$ | —O—C₆H₄—Cl (p) | S | 1.5215 |
| 17 | —CH(CH₃)—CH₂CH₃ | —$OC_2H_5$ | —$SC_3H_7$—n | S | 1.4977 |

| Example No. | | | | | |
|---|---|---|---|---|---|
| 18 | —$CH_2CH(CH_3)_2$ | —$OC_2H_5$ | —$SC_3H_7$—n | S | 1.4950 |
| 19 | —$(CH_2)_3$—$CH_3$ | —$OC_2H_5$ | —$SC_3H_7$—n | S | 1.4944 |
| 20 | —$(CH_2)_9$—$CH_3$ | —$OC_2H_5$ | —$SC_3H_7$—n | S | 1.4890 |
| 21 | 2-pyridyl | —$OC_2H_5$ | —$SC_3H_7$—n | S | 1.5402 |
| 22 | 3-pyridyl | —$OC_2H_5$ | —$SC_3H_7$—n | S | 1.5340 |
| 23 | —CH=$CH_2$ | —$OC_2H_5$ | —$SC_3H_7$—n | S | 1.5337 |
| 24 | —$CH_2$—C₆H₅ | —$OC_2H_5$ | —$SC_3H_7$—n | S | 1.5643 |
| 25 | —$C(CH_3)_3$ | —$OC_2H_5$ | —$SC_3H_7$—n | S | 1.5018 |
| 26 | 2,2-dimethylcyclopropyl—CO—$OC_2H_5$ | —$OC_2H_5$ | —$SC_3H_7$—n | S | 1.5003 |

TABLE-continued

| | R | R¹ | R² | X | Refractive index ($n_D^{20}$) |
|---|---|---|---|---|---|
| 27 | 2,2-dimethylcyclopropanecarbonyl-OCH₂-(3-phenoxyphenyl) | —OC₂H₅ | —SC₃H₇—n | S | 1.5483 |
| 28 | H | —OC₂H₅ | —SC₃H₇—n | S | 1.5101 |
| 29 | —CH₃ | —OC₂H₅ | —SC₃H₇—n | S | 1.5040 |
| 30 | 2-thienyl | —OC₂H₅ | —SC₃H₇—n | S | 1.5665 |
| 31 | 3-thienyl | —OC₂H₅ | —SC₃H₇—n | S | 1.5515 |
| 32 | —C₃H₇—iso | —CH₃ | —SC₃H₇—n | S | 1.5180 |
| 33 | —C₃H₇—iso | —OC₂H₅ | —OC₂H₅ | S | 1.4640 |
| 34 | —C₃H₇—iso | —C₂H₅ | —S—CH(CH₃)—CH₂—CH₃ | S | 1.5150 |
| 35 | —C₃H₇—iso | —OC₂H₅ | —NH—C₃H₇—iso | S | 1.4567 |
| 36 | —C₃H₇—iso | —OC₂H₅ | —SC₃H₇—n | S | 1.5035 |
| 37 | —CH=CH—CH₃ | —OC₂H₅ | —SC₃H₇—n | S | 1.5290 |
| 38 | —CH(CH₃)—phenyl | —OC₂H₅ | —SC₃H₇—n | S | 1.5410 |
| 39 | 4-chlorophenyl | —OC₂H₅ | —OC₂H₅ | S | 1.5303 |
| 40 | 4-chlorophenyl | —C₂H₅ | —OC₂H₅ | S | 1.5431 |
| 41 | 4-chlorophenyl | —OC₂H₅ | —SC₃H₇—n | S | 1.5559 |
| 42 | 4-methylphenyl | —OC₂H₅ | —SC₃H₇—n | S | 1.5436 |
| 43 | —C₃H₇—iso | —OC₂H₅ | —SC₃H₇—n | S | 1.4990 |
| 44 | 4-chlorophenyl | —CH₃ | —OCH₂CF₃ | S | 1.5195 |
| 45 | —CH(CH₃)—phenyl | —N(CH₃)₂ | —SCH₃ | S | 1.5453 |

TABLE-continued

| | R | R¹ | R² | X | Refractive index ($n_D^{20}$) |
|---|---|---|---|---|---|
| 46 | -CH(CH₃)-C₆H₅ | -SC₃H₇n | -SCH₂CH₂SC₂H₅ | S | 1.5720 |
| 47 | -CH(CH₃)-C₆H₅ | -OC₂H₅ | -SCH(CH₃)CH₂CH₃ | S | 1.5500 |
| 48 | -CH(CH₃)-C₆H₅ | -OC₂H₅ | -SCH₂CH₂SC₂H₅ | S | 1.5640 |
| 49 | -CH₃ | -C₂H₅ | -S-CH(CH₃)-C₂H₅ | S | 1.5226 |
| 50 | -C₂H₅ | -C₂H₅ | -S-CH(CH₃)-C₂H₅ | S | 1.5170 |
| 51 | -CH=CH-CH₃ | -C₂H₅ | -S-CH(CH₃)-C₂H₅ | S | 1.5250 |
| 52 | 2,2-dimethyl-3,3-dichlorocyclopropyl | -OC₂H₅ | -OC₂H₅ | O | 1.4575 |
| 53 | 2,2-dimethyl-3,3-dichlorocyclopropyl | -OC₂H₅ | -SC₃H₇-n | O | 1.4703 |
| 54 | 2,2-dimethyl-3,3-dichlorocyclopropyl | -OC₂H₅ | -SC₃H₇-n | S | 1.5103 |
| 55 | 2,2-dimethyl-3,3-dichlorocyclopropyl | -OC₂H₅ | -OC₂H₅ | S | 1.4858 |
| 56 | -C(CH₃)₃ | -C₂H₅ | -S-CH(CH₃)-C₂H₅ | S | 1.5130 |
| 57 | cyclohexyl | -C₂H₅ | -S-CH(CH₃)-C₂H₅ | S | 1.5218 |
| 58 | -C₆H₄-Cl (p) | -C₂H₅ | -S-CH(CH₃)-C₂H₅ | S | 1.5643 |
| 59 | -C₃H₇-n | -C₂H₅ | -S-CH(CH₃)-C₂H₅ | S | 1.5083 |

TABLE-continued

| | R | R¹ | R² | X | Refractive index ($n_D^{20}$) |
|---|---|---|---|---|---|
| 60 | —CH₂—CH(CH₃)₂ | —C₂H₅ | —S—CH(CH₃)—C₂H₅ | S | 1.5040 |
| 61 | —(CH₂)₃—CH₃ | —C₂H₅ | —S—CH(CH₃)—C₂H₅ | S | 1.5035 |
| 62 | —CH₂—OCH₃ | —C₂H₅ | —S—CH(CH₃)—C₂H₅ | S | 1.5260 |
| 63 | 3,4-methylenedioxyphenyl | —C₂H₅ | —S—CH(CH₃)—C₂H₅ | S | 1.5668 |
| 64 | —CH₃ | —OC₂H₅ | —SC₃H₇—n | O | 1.4600 |
| 65 | —C₃H₇—i | —OC₂H₅ | —SC₃H₇—n | O | 1.4565 |
| 66 | —C₃H₇—i | —C₂H₅ | —S—CH(CH₃)—C₂H₅ | O | 1.4805 |
| 67 | —C₃H₇—i | —C₂H₅ | —SC₃H₇—n | S | 1.5088 |
| 68 | —H | —C₂H₅ | —S—CH(CH₃)—C₂H₅ | S | 1.5352 |
| 69 | —C₃H₇—i | —C₂H₅ | —S—C₃H₇—i | S | 1.5069 |
| 70 | —C₃H₇—i | —C₆H₅ | —S—CH(CH₃)—C₂H₅ | S | 1.5970 |
| 71 | —C₃H₇—i | —CH₃ | —S—CH(CH₃)—C₂H₅ | S | 1.5078 |
| 72 | —C₃H₇—i | —C₂H₅ | —S—C₂H₅ | S | 1.5102 |
| 73 | —CH₂—CH₂—C₆H₅ | CH₃ | S—CH(CH₃)—C₂H₅ | S | 1.5460 |
| 74 | 4-OCF₃-C₆H₄— | C₂H₅ | S—CH(CH₃)—C₂H₅ | S | 1.5097 |
| 75 | 2,2-dichloro-3,3-dimethylcyclopropyl | C₂H₅ | S—CH(CH₃)—C₂H₅ | S | 1.5182 |
| 76 | 4-OCF₃-C₆H₄— | C₂H₅O | S—C₃H₇—n | S | 1.5082 |
| 77 | 4-OCF₃-C₆H₄— | C₂H₅O | SC₃H₇—n | O | 1.4720 |

TABLE-continued

| | R | R¹ | R² | X | Refractive index ($n_D^{20}$) |
|---|---|---|---|---|---|
| 78 | $CH_2-N(CH_3)_2$ | $C_2H_5$ | $S-\underset{\underset{CH_3}{\mid}}{CH}-C_2H_5$ | S | 1.5397 |
| 79 | $CH_2-N(CH_3)_2$ | $C_2H_5O$ | $SC_3H_7-n$ | S | 1.5443 |
| 80 | $\underset{\underset{CH_3}{\mid}}{CH}-C_2H_5$ | $C_2H_5$ | $S-\underset{\underset{CH_3}{\mid}}{CH}-C_2H_5$ | S | 1.5053 |
| 81 | 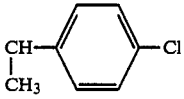 | $C_2H_5O$ | $SC_3H_7-n$ | S | |
| 82 | 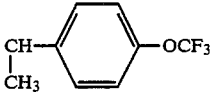 | $C_2H_5O$ | $SC_3H_7-n$ | S | |

(compounds 81 and 82 not actually synthesized)

As already indicated above, the new active compounds are superior to the known active compounds obtainable according to the invention.

The pesticidal activity of the compounds of this invention is illustrated by the following examples wherein the compounds according to the present invention are each identified by the number (given in brackets) from Example 1 and the table.

The known comparison compound is O,O-diethyl-O-(1-cyanoethyl)-thiophosphoric acid ester.

EXAMPLE 2

Laphygma test
Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified period of time, the destruction in % was determined. 100% meant that all the caterpillars have been killed; 0% meant that none of the caterpillars have been killed.

In this test, after 3 days, the "comparison compound" showed a degree of destruction of 0% at an active compound concentration of 0.1%, while, under the same conditions, the compounds (1), (2), (7), (8), (11), (12), (14), (15), (17), (18), (24), (25), (26), (28), (29), (32), (34), (36), (38), (41), (42) and (43), for example, showed a degree of destruction of 100%.

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Phaseolus vulgaris*) which were heavily infested with the common spider mite or two-spotted spider mite (*Tetranychus urticae*) in all stages of development were treated by being dipped into the preparation of the active compound of the desired concentration.

After the specified period of time, the destruction in % was determined. 100% meant that all the spider mites had been killed; 0% meant that none of the spider mites had been killed.

In this test, after 2 days, the "comparison compound" showed a degree of destruction of 0% at an active compound concentration of 0.1%, while, under the same conditions, the compounds (1), (11), (12), (14), (17), (18), (24), (25), (26), (32), (34), (36), (38) and (43), for example, showed a degree of destruction of 100%.

EXAMPLE 4

Critical concentration test/soil insects
Test insect: Phorbia antiqua grubs (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l), being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and live test insects. The degree of effectiveness was 100% if all the test insects had been killed and was 0% if just as many test insects were still alive as in the case of the untreated control.

In a test at an active compound concentration of 5 ppm, the "comparison compound" showed a degree of destruction of 0%, whilst the compounds (1), (17), (18), (29), (32), (34), (36), (38) and (43) showed a degree of destruction of 100%.

EXAMPLE 5

Test with parasitic fly larvae
Solvent 35 parts by weight of ethylene polyglycol monomethyl ether
Emulsifier: 35 parts by weight of nonylphenol polyglycol ether To produce a suitable preparation of active compound, 30 parts by weight of the active substance in question were mixed with the stated amount of solvent which contained the abovementioned proportion of emulsifier and the concentrate thus obtained was diluted with water to the desired concentration.

About 20 fly larvae (*Lucilia cuprina*) were introduced into a test tube which contained approx. 2 cm³ of horse muscle. 0.5 ml of the preparation of active compound was applied to this horse meat. After 24 hours, the degree of destruction in % was determined. 100% means that all the larvae had been killed and 0% meant that none of the larvae had been killed.

In a test with an active compound concentration of 100 ppm, the compounds (1), (14), (17), (18), (19), (29), (32), (34), (36), (37) and (43), for example, showed a 100% destruction.

It will be appreciated that the instant specification and examples are set forth by way of illustration and not limitation, and that various modifications and changes may be made without departing from the spirit and scope of the present invention.

We claim:

1. A cyanohydrin phosphonate of the formula

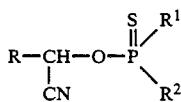

in which
R is a hydrogen atom, an alkyl radical which is optionally substituted by halogen, $C_1$ to $C_4$ alkoxy, $C_1$ to $C_4$ alkylthio or $C_1$-$C_4$-alkylamino and which has 1 to 20 carbon atoms, an optionally halogen-substituted $C_2$ to $C_5$ alkenyl or $C_2$ to $C_5$ alkynyl radical, a $C_3$ to $C_8$ cycloalkyl radical which is optionally substituted by $C_1$ to $C_4$ alkyl, $C_2$ to $C_4$ alkoxycarbonyl, phenoxybenzyloxycarbonyl and/or halogen, a phenyl-$C_1$ or $C_2$ alkyl radical which is optionally substituted by halogen, optionally halogen-substituted $C_1$ to $C_4$ alkyl or optionally halogen-substituted $C_1$ to $C_4$ alkoxy, a phenyl radical which is optionally substituted by halogen, nitro, $C_1$ to $C_4$ alkyl, optionally halogen substituted $C_1$ to $C_4$ alkoxy, optionally halogen-substituted $C_1$ to $C_4$ alkylthio, trifluoromethyl and/or by optionally halogen substituted $C_1$ or $C_2$ alkylenedioxy, or a furyl, thienyl or pyridyl radical, $R^1$ is an optionally halogen-substituted radical selected from $C_1$ to $C_5$ alkoxy, phenoxy, benzyloxy, $C_1$ to $C_5$ alkylthio, $C_3$ to $C_5$ alkenylthio, $C_3$ to $C_5$ alkynylthio, phenylthio, benzylthio and $C_1$ to $C_5$ alkylamino (monoalkylamino or dialkylamino), and $R^2$ is an optionally halogen-or $C_1$ to $C_4$ alkylthio-substituted radical selected from $C_1$ to $C_5$ alkyl and phenyl 2. A cyanohydrin phosphonate according to claim 1, in which
R is a hydrogen atom, an alkyl radical which is optionally substituted by fluorine, chlorine, methoxy, methylthio or dimethylamino and which has 1 to 10 carbon atoms, a $C_2$ to $C_5$ alkenyl, a $C_3$ to $C_6$ cycloalkyl radical which is optionally substituted by chlorine and/or methyl, a phenyl-$C_1$ or $C_2$ alkyl radical which is optionally substituted by chlorine or trifluoromethoxy, a phenyl radical which is optionally substituted by fluorine, chlorine, nitro, methyl, methoxy, trifluoromehoxy, trifluoromethyl and/or methylenedioxy, a thienyl radical or a pyridyl radical, $R^1$ is an optionally fluorine-substituted or chlorine-substituted radical selected from $C_1$ to $C_5$ alkoxy, phenoxy, benzyloxy, $C_1$ to $C_5$ alkylthio and $C_1$ to $C_5$ alkylamino (monoalkylamino or dialkylamino), and $R^2$ is an optionally fluorine- or chlorine- or ethylthio-substituted radical selected from $C_1$ to $C_5$ alkyl and phenyl.

3. A compound according to claim 1, wherein such compound is O-(1-cyanoethyl)-S-sec.-butyldithioethanephosphonic acid ester of the formula

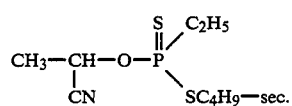

4. A compound according to claim 1, wherein such compound is O-(1-cyanopropyl)-S-sec.-butyldithioethanephosphonic acid ester of the formula

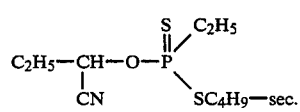

5. A compound according to claim 1, wherein such compound is O-(1-cyano-butyl)-S-sec.-butyldithioethanephosphonic acid ester of the formula

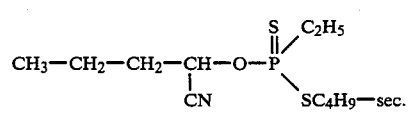

6. A compound according to claim 1, wherein such compound is O-(1-cyano-2-methyl-propyl)-S-sec.-butyldithioethanephosphonic acid ester of the formula

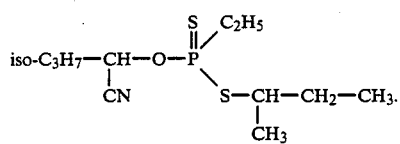

7. A compound according to claim 1, wherein such compound is O-(1-cyano-2,2-dimethylpropyl)-S-sec.-butyldithioethanephosphonic acid ester of the formula

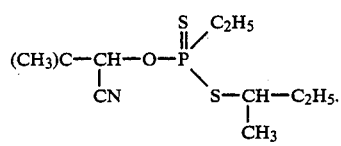

8. A compound according to claim 1, wherein such compound is O-[(2,2-dichloro-3,3-dimethyl-cyclopropyl)-cyanomethyl]-S-sec.-butyl-dithioethanephosphonate of the formula

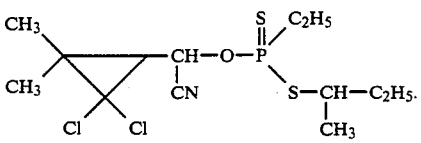

9. A pesticidal composition comprising a pesticidally effective amount of a compound according to claim 1 in admixture with a diluent.

10. A method of combating pests comprising applying to the pests, or to a habitat thereof, a pesticidally effective amount of a compound according to claim 1.

11. The method according to claim 10, wherein such compound is
O-(1-cyanoethyl)-S-sec.-butyldithioethanephosphonic acid ester,
O-(1-cyanopropyl)-S-sec.-butyldithioethanephosphonic acid ester,
O-(1-cyano-butyl)-S-sec.-butyldithioethanephosphonic acid ester,
O-(1-cyano-2-methyl-propyl)-S-sec.-butyldithioethanephosphonic acid ester,
O-(1-cyano-2,2-dimethylpropyl)-S-sec.-butyldithioethanephosphonic acid ester or
O-[(2,2-dichloro-3,3-dimethyl-cyclopropyl)-cyanomethyl]-S-sec.-butyl-dithioethanephosphonate.

* * * * *